(12) United States Patent
Zheng et al.

(10) Patent No.: US 12,090,054 B1
(45) Date of Patent: Sep. 17, 2024

(54) ANCHOR DELIVERY DEVICE FOR REPAIRING HEART VALVE

(71) Applicant: CREATIVE MEDTECH (BEIJING) CO., LTD, Beijing (CN)

(72) Inventors: Wei Zheng, Beijing (CN); Wuen Han, Beijing (CN); Fan Yang, Beijing (CN)

(73) Assignee: CREATIVE MEDTECH (BEIJING) CO., LTD, Beijing (CN)

( * ) Notice: Subject to any disclaimer, the term of this patent is extended or adjusted under 35 U.S.C. 154(b) by 0 days.

(21) Appl. No.: 18/431,989

(22) Filed: Feb. 4, 2024

(30) Foreign Application Priority Data

Jul. 5, 2023 (CN) .......................... 202310814392.4

(51) Int. Cl.
*A61F 2/24* (2006.01)
(52) U.S. Cl.
CPC .... *A61F 2/2466* (2013.01); *A61F 2220/0016* (2013.01)
(58) Field of Classification Search
CPC .............................................. A61F 2220/0016
See application file for complete search history.

(56) References Cited

U.S. PATENT DOCUMENTS

| 2004/0148020 A1 | 7/2004 | Vidlund et al. |
| 2007/0150000 A1 | 6/2007 | Osypka |
| 2009/0012557 A1 | 1/2009 | Osypka |
| 2012/0136200 A1 | 5/2012 | Miraki |
| 2014/0107755 A1 | 4/2014 | Ollivier |
| 2020/0178956 A1 | 6/2020 | Mitelberg et al. |
| 2020/0330228 A1 | 10/2020 | Anderson et al. |
| 2021/0220138 A1* | 7/2021 | Edmiston ............... A61F 2/2457 |

FOREIGN PATENT DOCUMENTS

| CA | 3126935 A1 | 7/2020 |
| CA | 3165008 A1 | 7/2021 |
| CN | 113040978 A | 6/2021 |
| CN | 114681132 A | 7/2022 |

(Continued)

OTHER PUBLICATIONS

Notice of Allowance of counterpart Chinese Patent Application No. 202310814392.4 issued on Aug. 28, 2023.

(Continued)

*Primary Examiner* — Brian A Dukert
*Assistant Examiner* — Rebecca Lynee Zimmerman

(57) ABSTRACT

The present invention provides an anchor delivery device for repairing a heart valve, and relates to the technical field of medical instruments. The system comprises a bend adjustable tube assembly, an anchor delivery assembly, a suture locking mechanism, and a puncture assembly. The anchor delivery assembly is mounted in the bend adjustable tube assembly; the suture locking mechanism is connected to an anchor, and is provided with a guide portion located in the anchor; and the puncture assembly is mounted in an anchor delivery tube, and a puncture needle body of the puncture assembly penetrates the guide portion and is radially limited by the guide portion. According to the present invention, the puncture accuracy of the puncture needle body and the stability thereof after puncture can be ensured, and the accuracy and stability of the subsequent implantation of the anchor are improved.

7 Claims, 10 Drawing Sheets

(56) References Cited

FOREIGN PATENT DOCUMENTS

| | | | |
|---|---|---|---|
| CN | 115243625 | A | 10/2022 |
| CN | 115399921 | A | 11/2022 |
| CN | 115955942 | A | 4/2023 |
| CN | 219070805 | U | 5/2023 |
| CN | 116236261 | A | 6/2023 |
| CN | 116269941 | A | 6/2023 |

OTHER PUBLICATIONS

First Office Action of counterpart Chinese Patent Application No. 202310814392.4 issued on Aug. 11, 2023.
Extended European Search Report of Counterpart European Patent Application No. 24155695.0 issued on Jun. 26, 2024.

* cited by examiner

ANCHOR DELIVERY DEVICE FOR REPAIRING HEART VALVE

CROSS REFERENCE TO RELATED APPLICATIONS

The present application claims the benefit of Chinese Patent Application No. 202310814392.4 filed on Jul. 5, 2023, the contents of which are incorporated herein by reference in their entirety.

TECHNICAL FIELD

The present invention relates to the technical field of medical devices, and in particular, to an anchor delivery device for repairing a heart valve.

BACKGROUND ART

Heart valve annulus repair surgery is a means for treating structural heart diseases, and mainly falls into edge-to-edge repair, valve annulus repair, and chordae tendineae repair according to methods. During valve annulus repair, an anchor needed to support an entire repair structure needs to be accurately and reliably delivered into a required position. The anchor is generally spiral and is similar in shape to a spring. An existing anchor delivery device for repairing a heart valve generally includes two functional assemblies. One of the functional assemblies is configured to implant an anchor or a fastening nail, which is located in an implant tube, into a valve annulus, and the other functional assembly functions to adjust the degree of bending of the implant tube so as to implant the anchor more accurately.

During an operation, the applicant has found that when the anchor in an implant tube is placed in an implantation position, the anchor cannot be stabilized in advance, the anchor is prone to unwanted displacement, and the stability of the anchor after implantation cannot be ensured. Moreover, since the anchor is implanted by ultrasonic imaging during the operation, the problem of unstable anchor delivery or anchor disengagement is aggravated. For this reason, the applicant initially added a puncture needle structure (see the applicant's Chinese earlier application No. 202310483312.1) to assist in implantation of an anchor. The puncture needle can be configured to fix a diaphragm to a valve annulus for repair, and is implanted in advance before the anchor is implanted, so that the entire anchor delivery device can be fixed to the valve annulus in advance, and then the anchor is implanted to assist in the positioning of the anchor, so as to improve the implantation accuracy and stability of the anchor. However, the applicant has found in the earlier patent application that the puncture needle directly punctures into the valve annulus by means of a proximal operating structure, and is located in the anchor and a spring tube implanted into the anchor. The puncture needle in this puncture form is very likely to come into contact with the anchor or the spring tube during puncturing or extension or retraction, thereby leading to a great reduction in stability and accuracy of puncture and affecting subsequent implantation of the anchor.

In addition, for an existing suture locking structure, after a locking suture is tightened, a locking suture between two suture locking mechanisms needs to be cut in order to prevent exposure of the locking suture which otherwise affects a surgery effect. This undoubtedly further increases the operation difficulty, prolongs the operation time, and causes a greater damage to a patient.

SUMMARY OF THE INVENTION

An embodiment of the present invention provides an anchor delivery device for repairing a heart valve, so as to solve at least some of the above problems.

According to the embodiment of the present invention, the anchor delivery device for repairing a heart valve is provided, the anchor delivery device comprising: a bend adjustable tube assembly; an anchor delivery assembly mounted in the bend adjustable tube assembly, wherein an anchor is mounted at a distal end of the anchor delivery assembly; a suture locking mechanism connected to the anchor and provided with a guide portion located in the anchor; and a puncture assembly mounted in an anchor delivery tube, wherein the puncture assembly comprises a puncture needle body, and the puncture needle body penetrates the guide portion and is radially limited by the guide portion.

In some implementations of the present invention, the guide portion comprises a guide cylinder, the guide cylinder is provided with an internal thread, and the puncture needle body is provided with an external thread connected to the internal thread.

In some implementations of the present invention, the puncture needle body comprises a tip portion and a rod portion that are integrally connected to each other, and the rod portion is provided with an external thread arranged in a length direction thereof.

In some implementations of the present invention, the extension length of the external thread on the puncture needle body is greater than or equal to twice the extension length of the internal thread on an inner wall of the guide cylinder.

In some implementations of the present invention, the suture locking mechanism comprises a suture locking tab connected to the guide portion; a plurality of first through holes for allowing the passage of the anchor is provided on a side of the suture locking tab connected to the guide portion; and a first suture passage hole configured for connection to a locking suture is provided on a side of the suture locking tab that faces away from the guide portion.

In some implementations of the present invention, a distal end of the bend adjustable tube assembly is provided with a sliding groove with an open end, and the suture locking tab is slidably mounted in the sliding groove.

In some implementations of the present invention, the anchor delivery device further comprises a suture locking assembly, wherein two suture locking mechanisms on two adjacent anchors are connected to each other via one locking suture, and the suture locking assembly is configured to adjust the length of the locking suture between the two suture locking mechanisms.

In some implementations of the present invention, the suture locking assembly comprises a suture locking device, a suture locking operation tube, and a suture locking operation cable; the locking suture penetrates a distal end of the suture locking device, and the suture locking operation tube is inserted into a proximal end of the suture locking device; and the suture locking operation cable passes through the suture locking operation tube, and is connected to the suture locking device, wherein the suture locking device is configured to adjust the length of the locking suture between the two suture locking mechanisms under the driving of the suture locking operation tube and the suture locking operation cable.

In some implementations of the present invention, the suture locking device comprises a suture locking rotary member, a suture retaining cylinder, and a pin; a distal end of the suture locking rotary member is provided with a second suture passage hole for allowing the passage of the locking suture, a proximal end of the suture locking rotary member is connected to the suture locking operation cable, the suture locking rotary member is provided with a first retaining hole in a radial direction, and the first retaining hole comprises a proximal sub-hole and a distal sub-hole that are in communication with each other; the suture retaining cylinder is sleeved on the suture locking rotary member, a distal end of the suture retaining cylinder is connected to the suture locking operation tube, a proximal end of the suture retaining cylinder is circumferentially provided with a plurality of suture retaining slots, and a side wall of the suture retaining cylinder is provided with a second retaining hole; the pin penetrates the first retaining hole and the second retaining hole; the suture locking device is configured to be actuatable between a first state and a second state; when the suture locking device is in the first state, the distal end of the suture locking rotary member is located outside the suture retaining cylinder, and the suture locking operation cable is capable of driving the suture locking rotary member to rotate so as to wind the locking suture around the suture locking rotary member; and when the suture locking device is switched from the first state to the second state, the suture retaining cylinder drives the pin located in the proximal sub-hole to move to the distal sub-hole, and two sides of the locking suture are arranged in two suture retaining slots in one-to-one correspondence.

In some implementations of the present invention, the proximal sub-hole is provided with a first elastic limiting portion for limiting the pin in the proximal sub-hole; and the distal sub-hole is provided with a second elastic limiting portion for limiting the pin in the distal sub-hole, wherein when the pin moves from the proximal sub-hole to the distal sub-hole, the first elastic limiting portion is deformed.

In the anchor delivery device for repairing a heart valve according to the embodiment of the present invention, the puncture assembly and the suture locking mechanism are provided, and the puncture needle body of the puncture assembly is connected to the guide portion of the suture locking mechanism, so as to guide the puncture needle body for puncturing by means of the guide portion, so that the puncture accuracy of the puncture needle body and the stability thereof after the puncturing can be ensured. The puncture needle body punctures into a part to be punctured by means of threaded rotation, so that the puncture needle body generates a rotary motion when linearly moving, facilitating the puncturing of the tip portion of the puncture needle body into a valve, thereby further improving the puncture efficiency and the puncture accuracy and stability of the puncture needle body during puncturing, providing better guidance and stabilization for subsequent implantation of anchors, and improving the accuracy and stability of the subsequent implantation of the anchors. In addition, with the provision of a novel suture locking assembly structure, there is no need to cut the locking suture, thus reducing the operation difficulty and the operation time.

BRIEF DESCRIPTION OF THE DRAWINGS

Features, advantages and technical effects of exemplary embodiments of the present invention will be described below with reference to accompanying drawings.

LIST OF REFERENCE SIGNS

100. Bend adjustable tube assembly; 110. Bend adjustable tube body; 120. Bend adjustable tube port; 121. Sliding groove; 1211. Snap-fit structure; 1212. Circular cutout; 200. Anchor delivery assembly; 210. Anchor delivery tube body; 220. Anchor delivery tube port; 221. First connecting port; 230. Anchor; 231. Second connecting port; 300. Suture locking mechanism; 310. Guide portion; 320. Suture locking tab; 321. First through hole; 322. First suture passage hole; 400. Puncture assembly; 410. Puncture needle body; 411. Tip portion; 412. Rod portion; 420. Puncture steel cable; 500. Suture locking assembly; 510. Suture locking device; 511. Suture locking rotary member; 5111. Second suture passage hole; 5112. First retaining hole; 51121. Proximal sub-hole; 51122. Distal sub-hole; 51123. First elastic limiting portion; 51124. Second elastic limiting portion; 512. Suture retaining cylinder; 5121. Suture retaining slot; 5122. Second retaining hole; 513. Pin; 520. Suture locking operation tube; 530. Suture locking operation cable.

DETAILED DESCRIPTION OF EMBODIMENTS

Implementations of the present invention will be further described in detail below with reference to the accompanying drawings and embodiments. The following detailed description of the embodiments and the accompanying drawings are used to illustrate the principle of the present invention by way of example and are not intended to limit the scope of the present invention. That is, the present invention is not limited to the described embodiments.

In order to better understand the present invention, embodiments of the present invention will be described below with reference to FIGS. 1 to 10.

Figure 1:
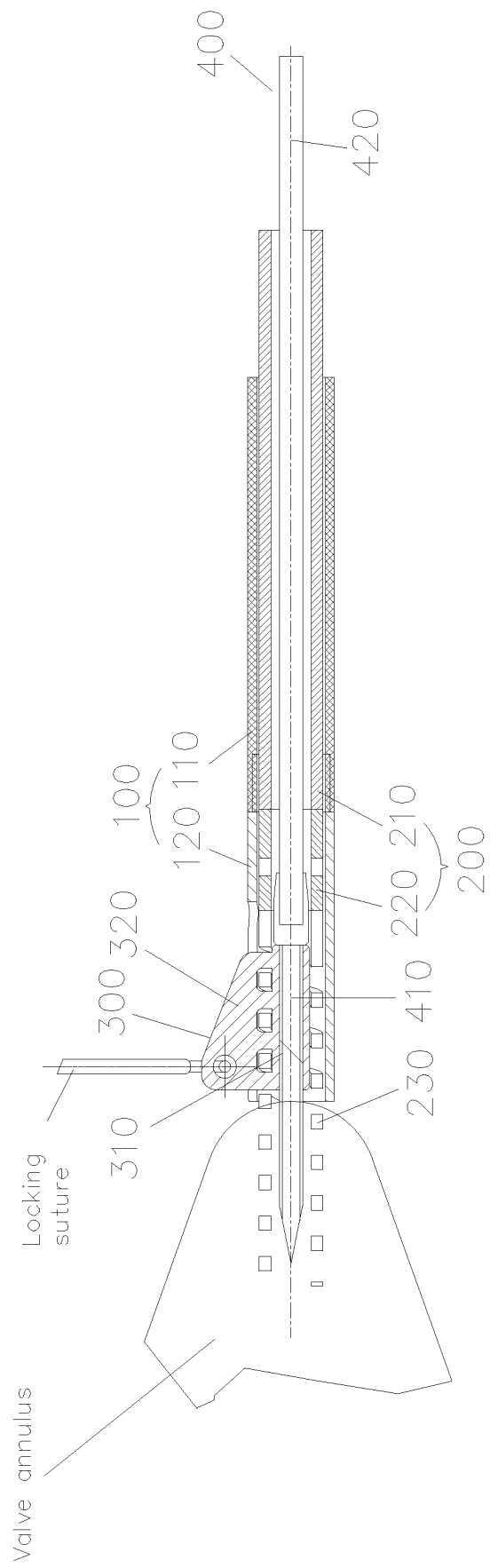
FIG. 1 is a schematic structural diagram of an anchor delivery device for repairing a heart valve according to an embodiment of the present invention.
Figure 2:
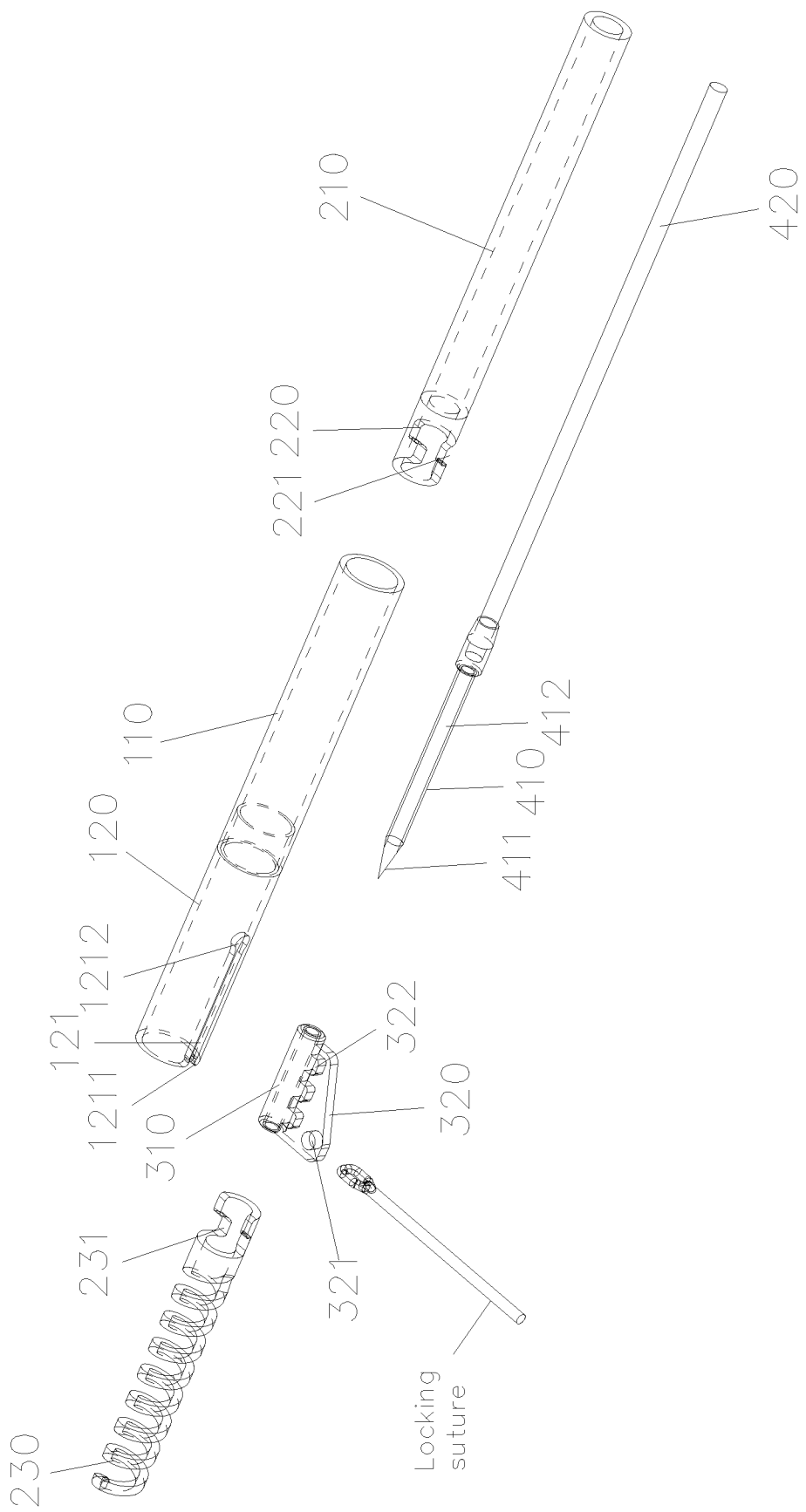
FIG. 2 is an exploded view of an anchor delivery device for repairing a heart valve according to an embodiment of the present invention.

FIG. 1 is a schematic structural diagram of an anchor delivery device for repairing a valve according to an embodiment of the present invention, and FIG. 2 is an exploded view of an anchor delivery device for repairing a valve according to an embodiment of the present invention.

As shown in FIGS. 1 and 2, the anchor delivery device for repairing a valve according to this embodiment mainly comprises a bend adjustable tube assembly 100, an anchor delivery assembly 200, a suture locking mechanism 300, a puncture assembly 400, and other functional assemblies.

Among the aforementioned functional assemblies, the bend adjustable tube assembly 100 in this embodiment comprises a bend adjustable tube body 110 and a bend adjustable tube port 120 that are integrally connected to each other, and the bend adjustable tube body 110 and the bend adjustable tube port 120 jointly achieve position adjustment and positioning of an anchor 230. The bend adjustable tube port 120 is made of a metal and is integrally connected to a bend adjustable tube by means of melting. A distal end of the bend adjustable tube port 120 is provided with a sliding groove 121 with an open end, and a distal end of the sliding groove 121 is provided with a snap-fit structure 1211. A circular cutout 1212 is used at a rear part of the sliding groove 121. The sliding groove 121 mainly functions to retain a suture locking tab 320 of the suture locking mechanism 300 before anchor delivery, can provide a certain space for the suture locking tab 320 to slide therein, and can allow the suture locking tab 320 to be detached from the bend adjustable tube assembly 100 after the anchor delivery.

Among the aforementioned functional assemblies, the anchor delivery assembly 200 in this embodiment is mounted in the bend adjustable tube assembly 100, and the anchor delivery assembly 200 comprises an anchor delivery tube body 210, an anchor delivery tube port 220 and an anchor 230 that are connected in sequence from a proximal end to a distal end. The anchor delivery tube body 210 in this embodiment is of a spring tube structure, and the anchor delivery tube port 220 is integrally connected to the anchor delivery tube body 210 by means of welding. The anchor delivery tube port 220 in this embodiment is also made of a metal material, and a front part of the anchor delivery tube port 220 is provided with a first connecting port 221 facing a tail part of the anchor 230, to facilitate the mounting and dismounting of the anchor 230. The anchor 230 in this embodiment is spiral, a middle part of the anchor 230 has an accommodating space, and a rear end of the anchor 230 is provided with a second connecting port 231 for docking with the first connecting port 221.

Among the aforementioned functional assemblies, the suture locking mechanism 300 in this embodiment comprises a suture locking tab 320 and a guide portion 310 that are integrally connected to each other. The suture locking tab 320 is connected to the anchor 230, and the guide portion 310 is located in the accommodating space in the middle part of the anchor 230. In this embodiment, suture locking mechanisms 300 cooperate with anchors 230 in one-to-one correspondence, that is, after a plurality of anchors 230 are implanted, each anchor 230 is provided with one suture locking mechanism 300, and two adjacent suture locking mechanisms 300 are connected to each other via a single locking suture.

The puncture assembly 400 in this embodiment is mounted in the anchor delivery tube body 210, and the puncture assembly 400 comprises a puncture needle body 410 and a puncture steel cable 420. In order to solve the aforementioned technical problems, in this embodiment, the puncture needle body 410 penetrates the guide portion 310 and is radially limited by the guide portion 310.

With this structural design, the puncture needle body 410 may be guided for puncturing by means of the guide portion 310, to ensure the puncture accuracy of the puncture needle body 410 and the stability thereof after the puncturing, thus providing better guidance and stabilization for subsequent implantation of anchors 230, and improving the accuracy and stability of the subsequent implantation of the anchors 230.

Referring to FIGS. 1 and 2 again, the guide portion 310 in this embodiment comprises a guide cylinder and an internal thread arranged on an inner wall surface of the guide cylinder. Correspondingly, the puncture needle body 410 in this embodiment is provided with an external thread connected to the internal thread.

Specifically, the puncture needle body 410 in this embodiment comprises a tip portion 411 and a rod portion 412 that are integrally connected to each other. The rod portion 412 is configured to be connected to the puncture steel cable 420, and the rod portion 412 is provided with an external thread arranged in a length direction thereof. When puncture is needed, the puncture steel cable 420 in this embodiment is driven to rotate by operating a puncture handle (not shown), then the puncture needle body 410 in this embodiment is driven to rotate, and the puncture needle body 410 can rotate to puncture into a part to be punctured under the action of threaded connection. With this puncture form, the puncture needle body can rotate when linearly moving, thus facilitating the puncturing of the tip portion 411 of the puncture needle body 410 into the valve, and further improving the puncture efficiency and the puncture accuracy and stability of the puncture needle body 410 during puncturing.

In some examples, the extension length of the external thread on the puncture needle body 410 in this embodiment may be designed to be greater than or equal to twice the extension length of the internal thread on the inner wall of the guide cylinder. In this way, the puncture needle body 410 can still be in threaded connection with the inner wall of the guide cylinder after a large number of rotations, so that the puncture needle body 410 in this embodiment can have more linear moving travel and increase the puncture depth.

Referring to FIGS. 1 and 2 again, it can be seen that the suture locking mechanism 300 in this embodiment comprises a suture locking tab 320 connected to the guide portion 310. Moreover, in this embodiment, a plurality of first through holes 321 for allowing the passage of the anchors 230 is provided on a side of the suture locking tab 320 that is connected to the guide portion 310, and a first suture passage hole 322 for connection to a locking suture is provided on a side of the suture locking tab 320 that faces away from the guide portion 310.

In order to achieve linear movement of the suture locking tab 320 and enable the suture locking tab 320 in this embodiment to be separated from the bend adjustable tube assembly 100, the distal end of the bend adjustable tube port 120 in this embodiment is provided with a sliding groove 121 with an open end, and the suture locking tab 320 is slidably mounted in the sliding groove 121, so that the linear movement of the suture locking tab 320 can be realized by means of the sliding groove 121, and the suture locking tab 320 can be easily separated from the bend adjustable tube assembly 100 by means of an opening.

Figure 3:
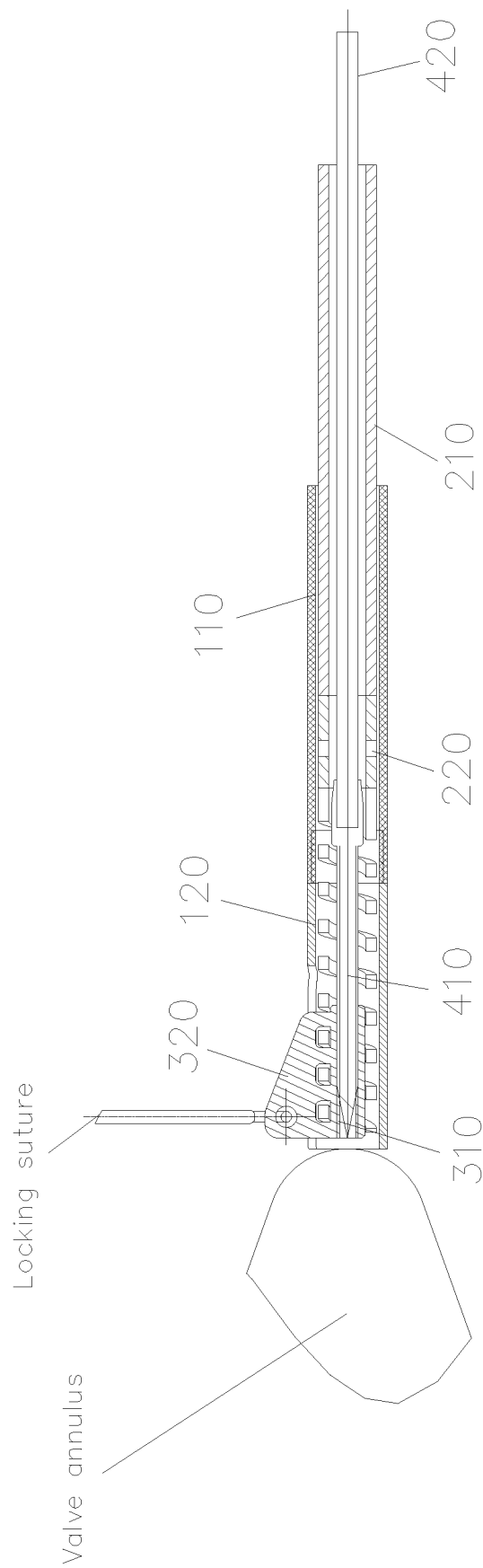
FIG. 3 is a schematic diagram of an anchor delivery device for repairing a heart valve at an anchor delivery position according to an embodiment of the present invention.

FIG. 3 is a schematic diagram of an anchor delivery device for repairing a valve at an anchor delivery position according to an embodiment of the present invention.

As shown in FIG. 3, an anchor 230 needs to be implanted during the valve repair surgery. Before the anchor 230 is implanted, the anchor delivery device of this embodiment needs to be first placed at the anchor delivery position. A specific operation is to adjust the distal end of the bend adjustable tube assembly 100 to an anchor delivery point of the anchor 230 under the driving of a bend adjustable tube handle (not shown).

Figure 4:
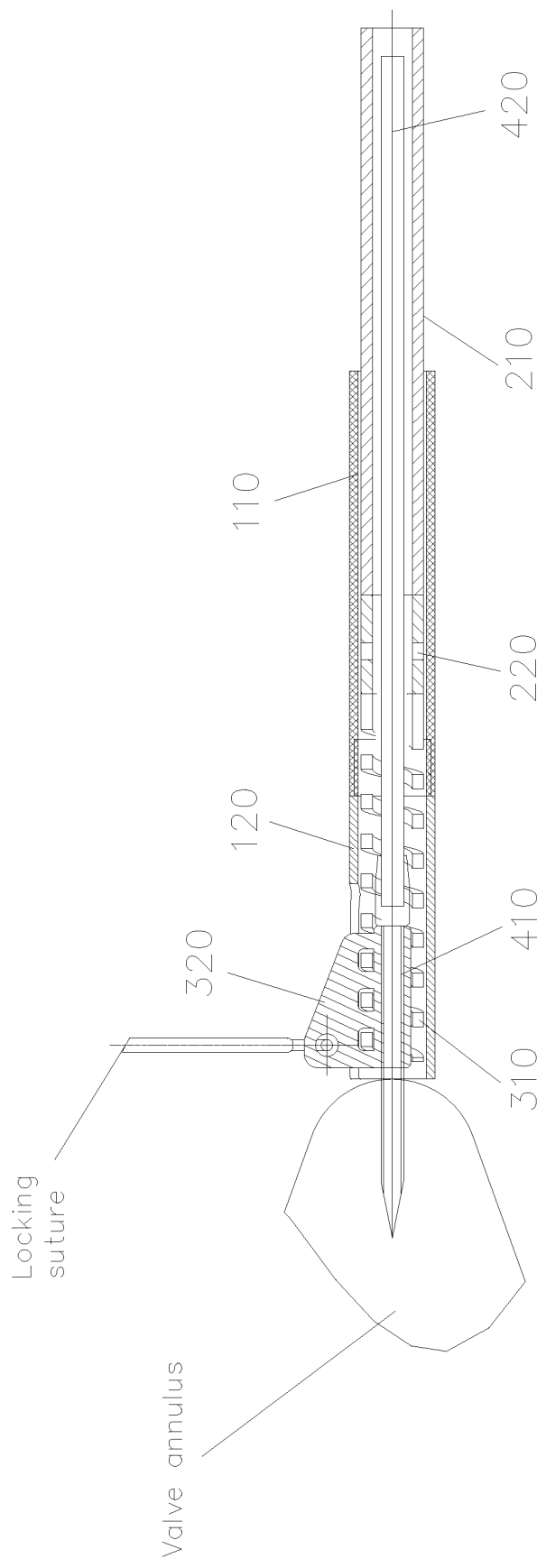
FIG. 4 is a schematic diagram of an anchor delivery device for repairing a heart valve according to an embodiment of the present invention with a puncture needle body penetrating into a valve annulus.

FIG. 4 is a schematic diagram of an anchor delivery device for repairing a valve according to an embodiment of the present invention with a puncture needle body penetrating into a valve annulus.

As shown in FIG. 4, after the operation of placing the anchor delivery device in FIG. 3 at the anchor delivery position is completed, the puncture needle body 410 in this embodiment is driven to rotate in the guide cylinder by means of the puncture steel cable 420. In this case, with the fit between the internal thread and the external thread, the puncture needle body 410 moves linearly while rotating and punctures into the valve annulus to form a state in the figure.

Figure 5:
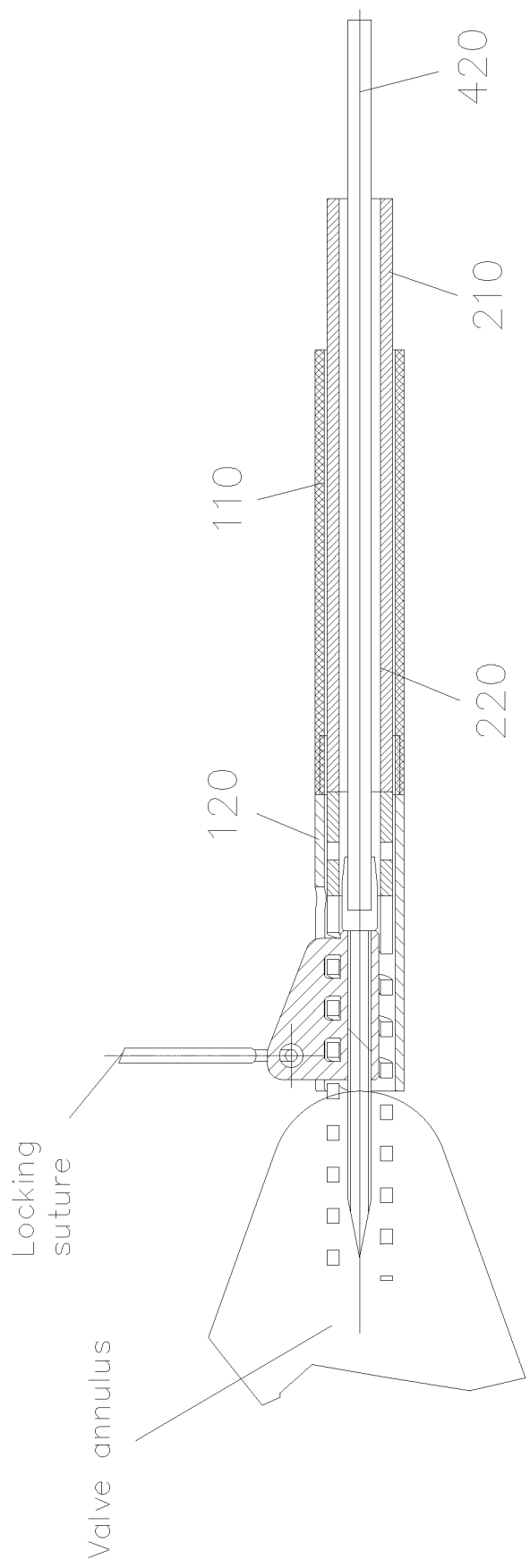
FIG. 5 is a schematic diagram of an anchor delivery device for repairing a heart valve according to an embodiment of the present invention with an anchor being implanted.

FIG. 5 is a schematic diagram of an anchor delivery device for repairing a valve according to an embodiment of the present invention with an anchor 230 being implanted.

As shown in FIG. 5, after the operation in FIG. 4 is completed, the puncture needle body has completed the relative fixation of the entire anchor delivery device to the valve. In this case, the anchor delivery tube body 210, the anchor delivery tube port 220 and the anchor 230 in this embodiment are driven to rotate by operating a handle, and the anchor 230 is rotatably delivered into the valve to complete the implantation of the anchor 230.

Figure 6:
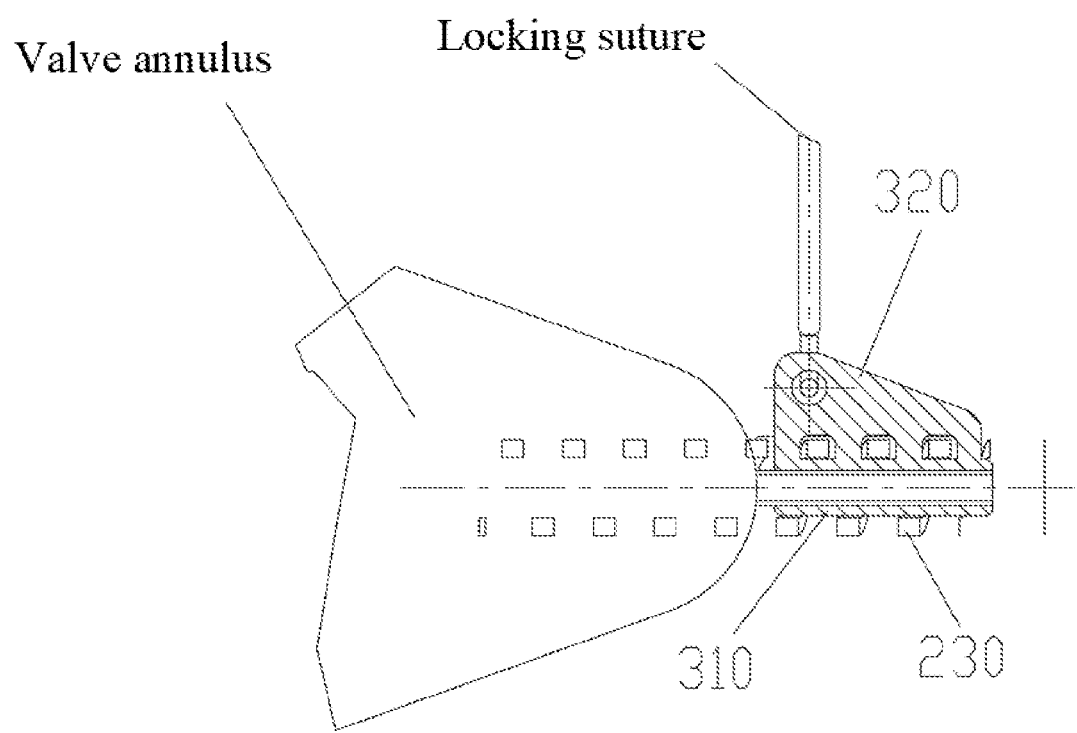
FIG. 6 is a schematic diagram showing that an anchor delivery device for repairing a heart valve is withdrawn after an anchor is implanted according to an embodiment of the present invention.

FIG. 6 is a schematic diagram showing that an anchor delivery device for repairing a valve is withdrawn after the anchor 230 is implanted according to an embodiment of the present invention.

As shown in FIG. 6, after the operation of implanting the anchor 230 is completed, the anchor delivery tube body 210 and the anchor delivery tube port 220 are reversely rotated, and the penetration of the puncture assembly 400 is removed, so that the anchor delivery tube body 210, the anchor delivery tube port 220, the puncture needle body 410, the puncture steel cable 420, the bend adjustable tube body 110, the bend adjustable tube port 120 and other structures in this embodiment are separated from the valve. At this time, structures remaining at the valve are only the anchor 230 and a locking mechanism.

After the aforementioned operation is completed, a locking suture between two adjacent locking mechanisms further needs to be tightened. Therefore, the anchor delivery device of this embodiment further comprises a suture locking assembly 500. Two suture locking mechanisms 300 on two adjacent anchors 230 are connected to each other via one locking suture, and the suture locking assembly 500 is configured to adjust the length of the locking suture between the two suture locking mechanisms 300.

The applicant has found that, for an existing suture locking structure, after a locking suture is tightened, a locking suture between two suture locking mechanisms 300 needs to be cut in order to prevent exposure of the locking suture which otherwise affects a surgery effect. This undoubtedly further increases the operation difficulty, prolongs the operation time, and causes a greater damage to a patient.

In view of this, this embodiment provides a novel suture locking assembly 500. With this structure, there is no need to cut the locking suture, thus reducing the operation difficulty and the operation time.

Figure 7:
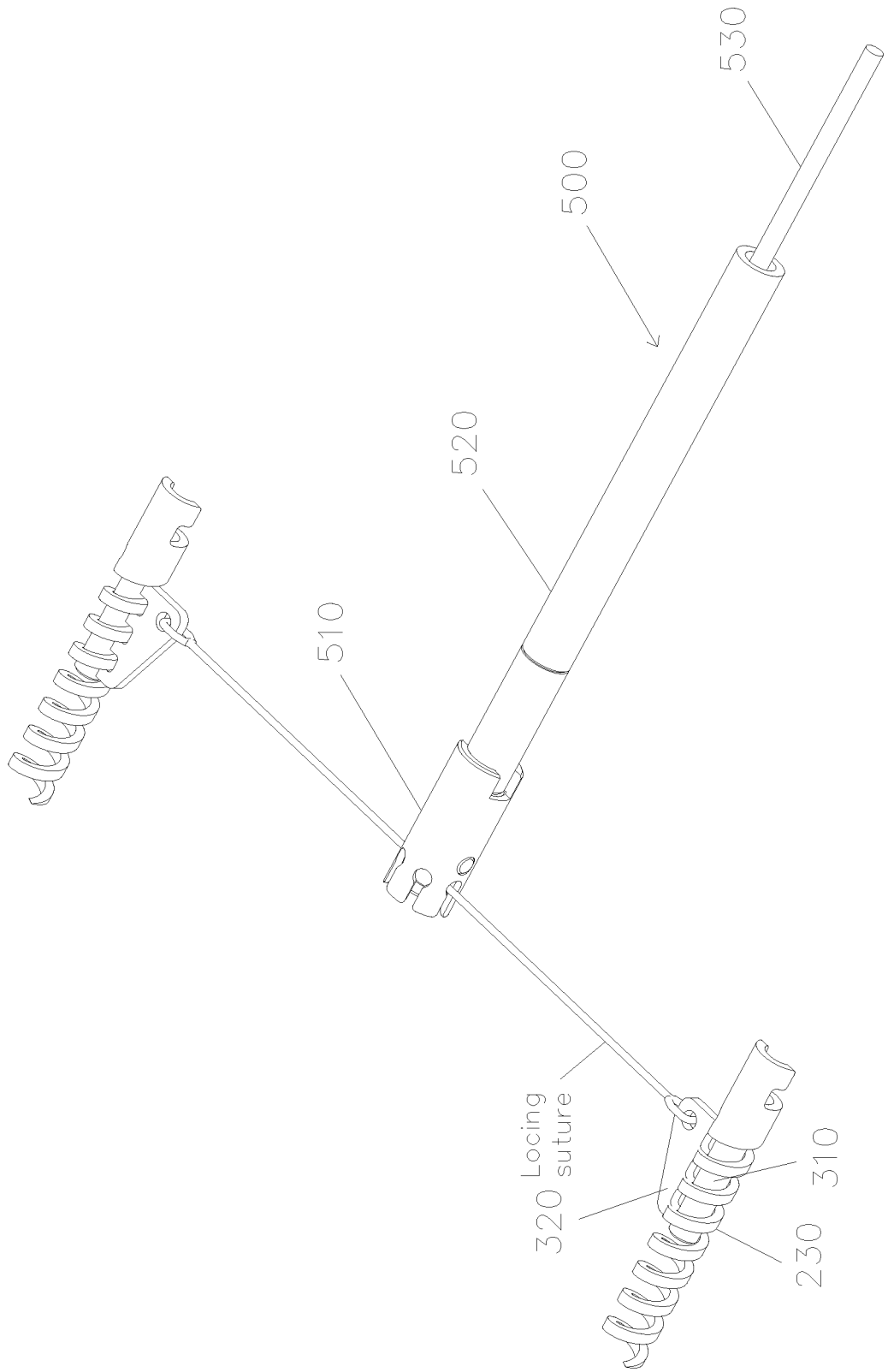
FIG. 7 is a schematic diagram of use of a suture locking assembly of an anchor delivery device for repairing a heart valve according to an embodiment of the present invention.
Figure 8:
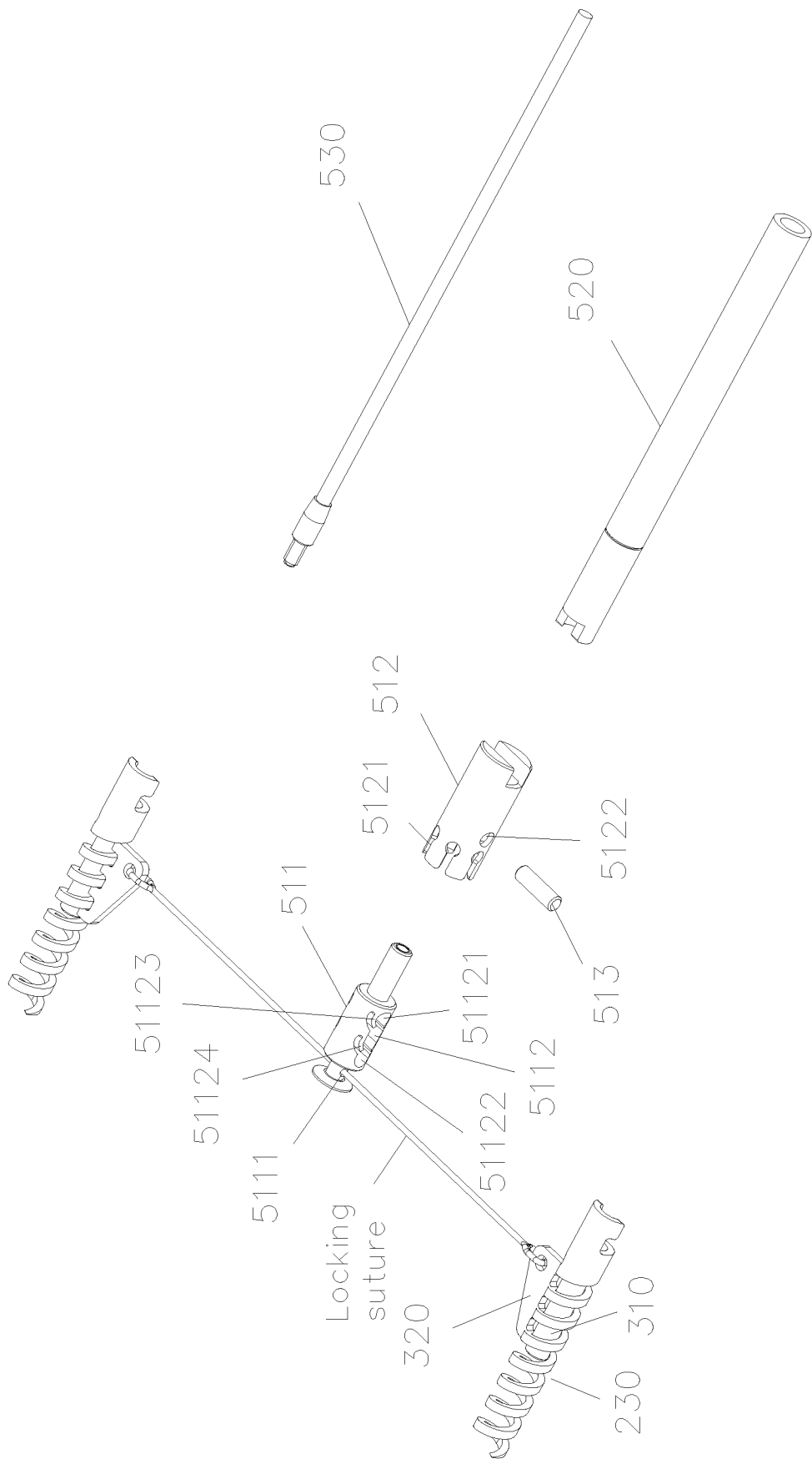
FIG. 8 is an exploded view of a suture locking assembly of an anchor delivery device for repairing a heart valve according to an embodiment of the present invention.

FIG. 7 is a schematic diagram of use of a suture locking assembly 500 of an anchor delivery device for repairing a valve according to an embodiment of the present invention, and FIG. 8 is an exploded view of a suture locking assembly 500 of an anchor delivery device for repairing a valve according to an embodiment of the present invention.

As shown in FIGS. 7 and 8, the suture locking assembly 500 according to this embodiment comprises a suture locking device 510, a suture locking operation tube 520, and a suture locking operation cable 530. The locking suture in this embodiment penetrates a distal end of the suture locking device 510, and the suture locking operation tube 520 in this embodiment is inserted into a proximal end of the suture locking device 510. The suture locking operation cable 530 in this embodiment passes through the suture locking operation tube 520, and is connected to the suture locking device 510. The suture locking device 510 in this embodiment is configured to adjust the length of the locking suture between the two suture locking mechanisms 300 under the driving of the suture locking operation tube 520 and the suture locking operation cable 530.

Specifically, the suture locking device 510 in this embodiment comprises a suture locking rotary member 511, a suture retaining cylinder 512, and a pin 513. The suture locking rotary member 511, the suture retaining cylinder 512 and the pin 513 in this embodiment are all generally columnar. A distal end of the suture locking rotary member 511 in this embodiment is provided with a second suture passage hole 5111 for allowing the passage of the locking suture, and a proximal end of the suture locking rotary member is connected to the suture locking operation cable 530. Moreover, the suture locking rotary member 511 in this embodiment is provided with a first retaining hole 5112 in a radial direction, and the first retaining hole 5112 comprises a proximal sub-hole 51121 and a distal sub-hole 51122 that are in communication with each other.

The suture retaining cylinder 512 in this embodiment is sleeved on the suture locking rotary member 511, a distal end of the suture retaining cylinder 512 is connected to the suture locking operation tube 520, a proximal end of the suture retaining cylinder 512 is circumferentially provided with a plurality of suture retaining slots 5121, and a side wall of the suture retaining cylinder 512 is provided with a second retaining hole 5122. The pin 513 in this embodiment penetrates the first retaining hole 5112 and the second retaining hole 5122.

The suture locking device 510 with the above structure is configured to be actuatable between a first state (non-suture-locking state) and a second state (suture locking state). When the suture locking device is in the first state, the distal end of the suture locking rotary member 511 in this embodiment is located outside the suture retaining cylinder 512. In this case, each suture retaining slot 5121 in this embodiment is not connected to the locking suture. Moreover, in this case, the suture locking operation cable 530 in this embodiment can drive the suture locking rotary member 511 to rotate, so as to wind the locking suture around the suture locking rotary member 511 to tighten the locking suture.

When the suture locking device is switched from the first state to the second state, the suture retaining cylinder 512 in this embodiment drives the pin 513 located in the proximal sub-hole 51121 to move to the distal sub-hole 51122, and two sides of the locking suture are arranged in two suture retaining slots 5121 in one-to-one correspondence. In this case, the suture locking operation cable 530 cannot drive the suture locking rotary member 511 to rotate, thereby completing the shortening and locking of the locking suture.

Figure 9:
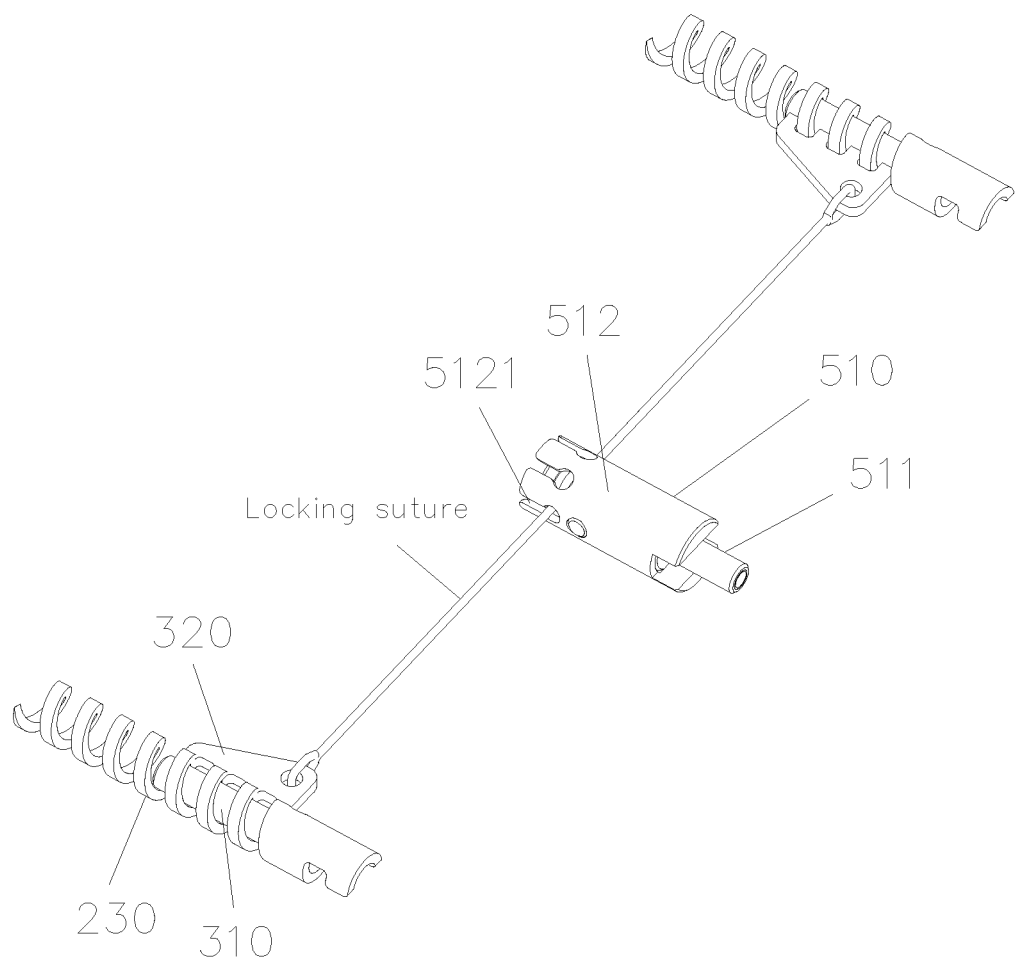
FIG. 9 is a schematic diagram of use of a suture locking device of a suture locking assembly of an anchor delivery device for repairing a heart valve according to an embodiment of the present invention.
Figure 10:
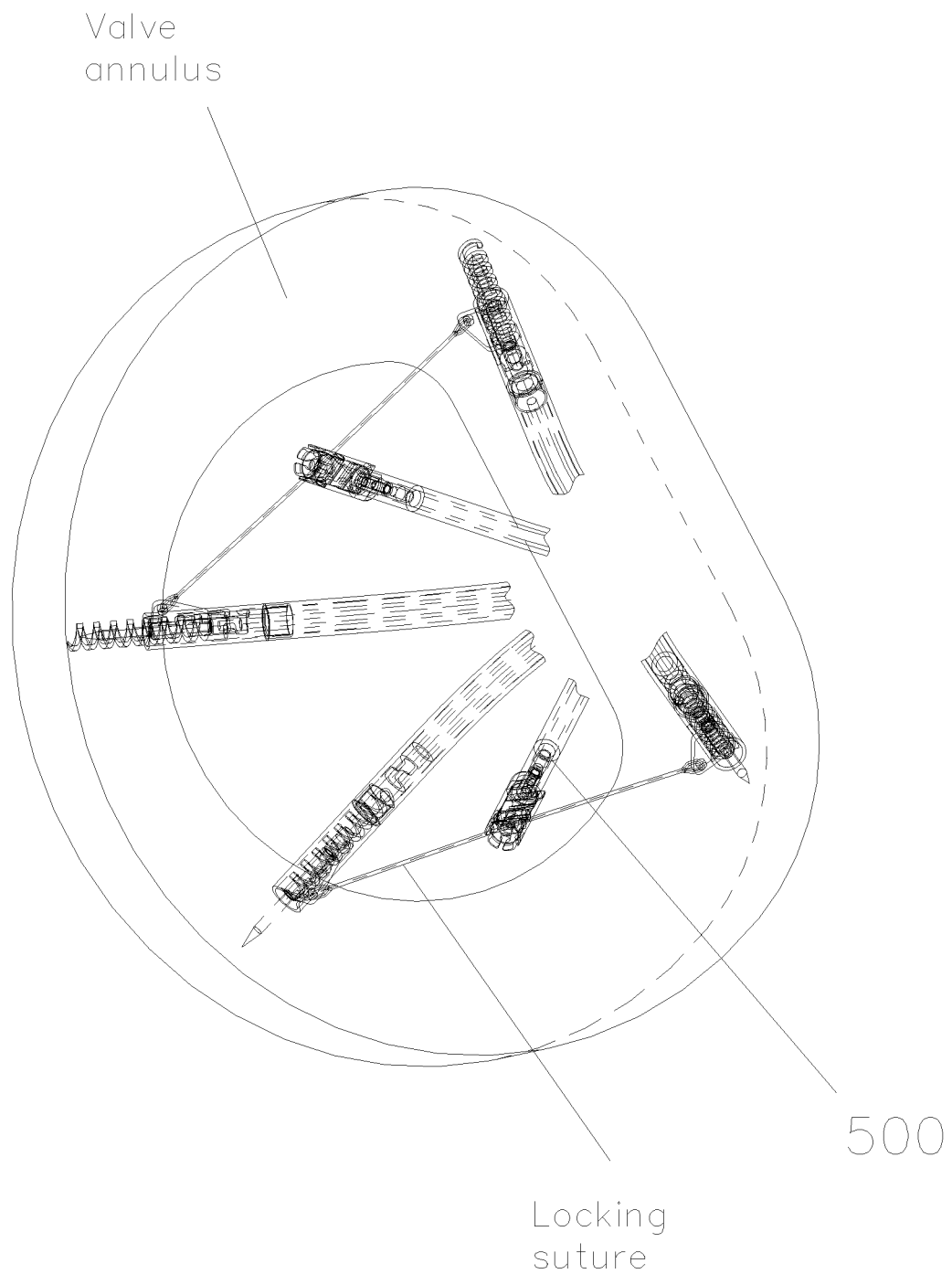
FIG. 10 is a schematic diagram of an anchor delivery device for repairing a heart valve according to an embodiment of the present invention after suture locking.

FIG. 9 is a schematic diagram of use of a suture locking device 510 of a suture locking assembly 500 of an anchor delivery device for repairing a valve according to an embodiment of the present invention.

As shown in FIG. 9, after the above switching from the first state to the second state is completed, the suture locking operation tube 520 and the suture locking operation cable 530 in this embodiment are operated again, such that the suture locking device 510 is separated from the suture locking operation tube 520 and the suture locking operation cable 530 in this embodiment, that is, only the suture locking device 510 is left in the human valve annulus. A plurality of anchors 230, a plurality of suture locking mechanisms 300 and a plurality of suture locking devices 510 form a state illustrated in FIG. 10.

Referring to FIG. 8 again, in order to achieve relative fixation of the suture locking rotary member 511 and the suture retaining cylinder 512 in this embodiment in the first state and the second state, the proximal sub-hole 51121 in this embodiment is further provided with a first elastic limiting portion 51123 for limiting the pin 513 in the proximal sub-hole 51121, and the distal sub-hole 51122 in this embodiment is further provided with a second elastic limiting portion 51124 for limiting the pin 513 in the distal sub-hole 51122.

In the first state, the first elastic limiting portion 51123 in this embodiment limits the pin 513 to the proximal sub-hole 51121. When the pin 513 moves from the proximal sub-hole 51121 to the distal sub-hole 51122 (when switching from the first state to the second state), the first elastic limiting portion 51123 is deformed. In the second state, the second elastic limiting portion 51124 in this embodiment limits the pin 513 to the distal sub-hole 51122.

It should be noted that the aforementioned "proximal end" in this embodiment refers to the end close to an operator during surgery, and the "distal end" refers to the end facing away from the operator during the surgery.

In the description of the present invention, unless otherwise stated, "a plurality of" means two or more. The orientation or position relationship indicated by a term such as "upper", "lower", "left", "right", "inner", and "outer" is only for the convenience of describing the present invention and simplifying the description, rather than indicating or implying that the device or element referred to must have a particular orientation or be constructed and operated in a particular orientation, and therefore should not be construed as a limitation on the present invention. In addition, the terms "first", "second" and "third" are for descriptive purposes only and should not be construed as indicating or implying relative importance.

The orientation terms in the following description all indicate directions shown in the drawings, and do not limit the specific structure in the present invention. In the description of the present invention, it should be further noted that unless otherwise explicitly specified and defined, the terms "mounting", "connecting" and "connection" should be understood in a broad sense, for example, they may be a fixed connection, a detachable connection, or an integrated connection; and may refer to a direct connection, or an indirect connection by means of an intermediate medium. For those of ordinary skill in the art, the specific meanings of the terms mentioned above in the present invention may be construed according to specific circumstances.

Although the present invention has been described with reference to the preferred embodiments, various modifications can be made, and equivalents can be provided to substitute for the components therein without departing from the scope of the present invention. In particular, the technical features mentioned in the embodiments can be combined in any manner, provided that there is no structural conflict. The present invention is not limited to the specific embodiments disclosed herein but includes all the technical solutions that fall within the scope of the claims.

What is claimed is:

1. An anchor delivery device for repairing a heart valve, characterized by comprising:
a bend adjustable tube assembly (100);
an anchor delivery assembly (200) mounted in the bend adjustable tube assembly (100), wherein an anchor (230) is mounted at a distal end of the anchor delivery assembly;
a suture locking mechanism (300) connected to the anchor (230) and provided with a guide portion (310) located in the anchor (230), wherein
the suture locking mechanism (300) comprises a suture locking tab (320) connected to the guide portion (310), a plurality of first through holes (321) for allowing the passage of the anchor (230) are provided on a side of the suture locking tab (320) connected to the guide portion (310), and a first suture passage hole (322) configured for connection to a locking suture is provided on a side of the suture locking tab (320) that faces away from the guide portion (310); and
a puncture assembly (400) mounted in the anchor delivery assembly (200), wherein the puncture assembly (400) comprises a puncture needle body (410), and the puncture needle body (410) penetrates the guide portion (310) and is radially limited by the guide portion (310);
the guide portion (310) comprises a guide cylinder, an inner wall of the guide cylinder is provided with an internal thread, and the puncture needle body (410) is provided with an external thread connected to the internal thread; the puncture needle body (410) comprises a tip portion (411) and a rod portion (412) that are integrally connected to each other, and the external thread is arranged in a length direction of the rod portion (412); and the puncture needle body (410) rotates to puncture into a part to be punctured under the action of threaded connection.

2. The anchor delivery device for repairing a heart valve according to claim 1, characterized in that
the extension length of the external thread on the puncture needle body (410) is greater than or equal to twice the extension length of the internal thread on the inner wall of the guide cylinder.

3. The anchor delivery device for repairing a heart valve according to claim 1, characterized in that
a distal end of the bend adjustable tube assembly (100) is provided with a sliding groove (121) with an open end, and the suture locking tab (320) is slidably mounted in the sliding groove (121).

4. The anchor delivery device for repairing a heart valve according to claim 1, characterized in that
it further comprises a suture locking assembly (500), wherein two suture locking mechanisms (300) on two adjacent anchors (230) are connected to each other via one locking suture, and the suture locking assembly (500) is configured to adjust the length of the locking suture between the two suture locking mechanisms (300).

5. The anchor delivery device for repairing a heart valve according to claim 4, characterized in that
- the suture locking assembly (500) comprises a suture locking device (510), a suture locking operation tube (520), and a suture locking operation cable (530);
- the locking suture penetrates a distal end of the suture locking device (510), and the suture locking operation tube (520) is inserted into a proximal end of the suture locking device (510); and
- the suture locking operation cable (530) passes through the suture locking operation tube (520), and is connected to the suture locking device (510),
- wherein the suture locking device (510) is configured to adjust the length of the locking suture between the two suture locking mechanisms (300) under the driving of the suture locking operation tube (520) and the suture locking operation cable (530).

6. The anchor delivery device for repairing a heart valve according to claim 5, characterized in that
- the suture locking device (510) comprises a suture locking rotary member (511), a suture retaining cylinder (512), and a pin (513);
- a distal end of the suture locking rotary member (511) is provided with a second suture passage hole (5111) for allowing the passage of the locking suture, a proximal end of the suture locking rotary member is connected to the suture locking operation cable (530), the suture locking rotary member (511) is provided with a first retaining hole (5112) in a radial direction, and the first retaining hole (5112) comprises a proximal sub-hole (51121) and a distal sub-hole (51122) that are in communication with each other;
- the suture retaining cylinder (512) is sleeved on the suture locking rotary member (511), a proximal end of the suture retaining cylinder (512) is connected to the suture locking operation tube (520), a distal end of the suture retaining cylinder (512) is circumferentially provided with a plurality of suture retaining slots (5121), and a side wall of the suture retaining cylinder (512) is provided with a second retaining hole (5122);
- the pin (513) penetrates the first retaining hole (5112) and the second retaining hole (5122);
- the suture locking device (510) is configured to be actuatable between a first state and a second state; when the suture locking device is in the first state, the distal end of the suture locking rotary member (511) is located outside the suture retaining cylinder (512), and the suture locking operation cable (530) is capable of driving the suture locking rotary member (511) to rotate so as to wind the locking suture around the suture locking rotary member (511); and when the suture locking device is switched from the first state to the second state, the suture retaining cylinder (512) drives the pin (513) located in the proximal sub-hole (51121) to move to the distal sub-hole (51122), and two sides of the locking suture are arranged in two suture retaining slots (5121) in one-to-one correspondence.

7. The anchor delivery device for repairing a heart valve according to claim 6, characterized in that
- the proximal sub-hole (51121) is provided with a first elastic limiting portion (51123) for limiting the pin (513) in the proximal sub-hole (51121); and
- the distal sub-hole (51122) is provided with a second elastic limiting portion (51124) for limiting the pin (513) in the distal sub-hole (51122),
- wherein when the pin (513) moves from the proximal sub-hole (51121) to the distal sub-hole (51122), the first elastic limiting portion (51123) is deformed.

\* \* \* \* \*